(12) United States Patent
Zhou

(10) Patent No.: US 8,852,919 B2
(45) Date of Patent: Oct. 7, 2014

(54) MICROFLUIDIC APPARATUS, METHOD, AND APPLICATIONS

(71) Applicant: Rheonix, Inc., Ithaca, NY (US)

(72) Inventor: Peng Zhou, Newtown, PA (US)

(73) Assignee: Rheonix, Inc., Ithaca, NY (US)

( * ) Notice: Subject to any disclaimer, the term of this patent is extended or adjusted under 35 U.S.C. 154(b) by 0 days.

(21) Appl. No.: 13/678,732

(22) Filed: Nov. 16, 2012

(65) Prior Publication Data

US 2013/0164826 A1 Jun. 27, 2013

Related U.S. Application Data

(60) Provisional application No. 61/561,007, filed on Nov. 17, 2011.

(51) Int. Cl.
*C12N 1/08* (2006.01)
*C12Q 1/68* (2006.01)
*C07H 1/08* (2006.01)

(52) U.S. Cl.
CPC ................ *C07H 1/08* (2013.01); *C12Q 1/6806* (2013.01)
USPC ........................................................ 435/270

(58) Field of Classification Search
None
See application file for complete search history.

(56) References Cited

U.S. PATENT DOCUMENTS

| | | | |
|---|---|---|---|
| 5,552,087 A * | 9/1996 | Zeheb et al. ................ | 252/408.1 |
| 6,248,535 B1 | 6/2001 | Danenberg et al. | |
| 6,469,159 B1 | 10/2002 | Belly et al. | |
| 6,544,798 B1 | 4/2003 | Christensen et al. | |
| 6,855,559 B1 | 2/2005 | Christensen et al. | |
| 7,067,325 B2 * | 6/2006 | Christensen et al. ......... | 436/503 |
| 7,410,753 B2 | 8/2008 | Hopkins et al. | |
| 7,544,471 B2 * | 6/2009 | Wang et al. .................. | 435/6.12 |
| 2004/0072305 A1 | 4/2004 | Erlander et al. | |

(Continued)

FOREIGN PATENT DOCUMENTS

| | | |
|---|---|---|
| WO | 2011008217 | 1/2011 |
| WO | 2011104032 | 9/2011 |

OTHER PUBLICATIONS

Kotorashvili, A. et al., Effective DNA/RNA Co-Extraction for Analysis of MicroRNAs, mRNAs, and Genomic DNA from Formalin-Fixed Paraffin-Embedded Specimens, PLoS One, Apr. 2012, vol. 7, Issue 4, e34683, pp. 1-11.

(Continued)

*Primary Examiner* — Patricia A Leith
*Assistant Examiner* — Erin M Bowers
(74) *Attorney, Agent, or Firm* — William Greener; Bond, Schoeneck & King, PLLC

(57) ABSTRACT

A microfluidic apparatus, method, and associated applications utilize and apply to a formalin-fixed paraffin-embedded (FFPE) tissue sample and performing a liquid-liquid extraction to remove the paraffin from the tissue sample prior to a nucleic acid purification step. A microfluidic device includes a dedicated liquid-liquid extraction process vessel, a nucleic acid purification process component, and a nucleic acid amplification reactor. A liquid-liquid extraction and nucleic acid purification kit includes a microfluidic device capable of performing both a liquid-liquid extraction process and a nucleic acid purification process, including a dedicated liquid-liquid extraction process vessel, an immiscible liquid or a precursor phase thereof disposed in the vessel, a nucleic acid purification process component, a nucleic acid amplification reactor fluidically, and a supply of reagents suitable to enable the liquid-liquid extraction process and the nucleic acid purification process.

5 Claims, 14 Drawing Sheets

(56) References Cited

U.S. PATENT DOCUMENTS

| | | |
|---|---|---|
| 2005/0142570 A1 | 6/2005 | Parthasarathy et al. |
| 2011/0092691 A1 | 4/2011 | Euting et al. |
| 2011/0245483 A1 | 10/2011 | Euting et al. |

OTHER PUBLICATIONS

Honda, K. et al., Clonal Analysis of the Epithelial Component of Warthin's Tumor, Human Pathology, vol. 31, No. 11, Nov. 2000, pp. 1377-1380.

Sato, Y. et al., Comparison of the DNA Extraction Methods for Polymerase Chain Reaction Amplification from Formalin-Fixed and Paraffin-Embedded Tissues, Diagnostic Molecular Pathology, 10(4), pp. 265-271, 2001.

Correnti, M. et al., Detection of human papillomaviruses of high oncogenic potential in oral squamous cell carcinoma in a Venezuelan population, Oral Diseases, 2004, 10, pp. 163-166.

Campos, P. et al., DNA Extraction from Formalin-Fixed Material, Ancient DNA: Methods and Protocols, Methods in Molecular Biology, vol. 840, DOI 10.1007/978-1-61779-516-9_11, 2012, pp. 81-85.

Gilbert, M. et al., The Isolation of Nucleic Acids from Fixed, Paraffin-Embedded Tissues—Which Methods Are Useful When?, PLos One, Jun. 2007, Issue 6, e537, pp. 1-12.

Longy, M. et al., Method for the Purification of Tissue DNA Suitable for PCR After Fixation with Bouin's Fluid, Diagnostic Molecular Pathology, 6(3), pp. 167-173, 1997.

Gilbert, M. et al., Multiple PCR with minisequencing as an effective high-throughput SNP typing method for formalin-fixed tissue, Electrophoresis, 2007, 28, pp. 2361-2367.

Lobo, A. et al., Protocol for the Use of Polymerase Chain Reaction in the Detection of Intraocular Large B-Cell Lymphoma in Ocular Samples, Journal of Molecular Diagnostics, vol. 9, No. 1, Feb. 2007, pp. 113-121.

International Search Report Form PCT/ISA/220, International Application No. PCT/US2012/065452, pp. 1-9, Mar. 28, 2013.

* cited by examiner

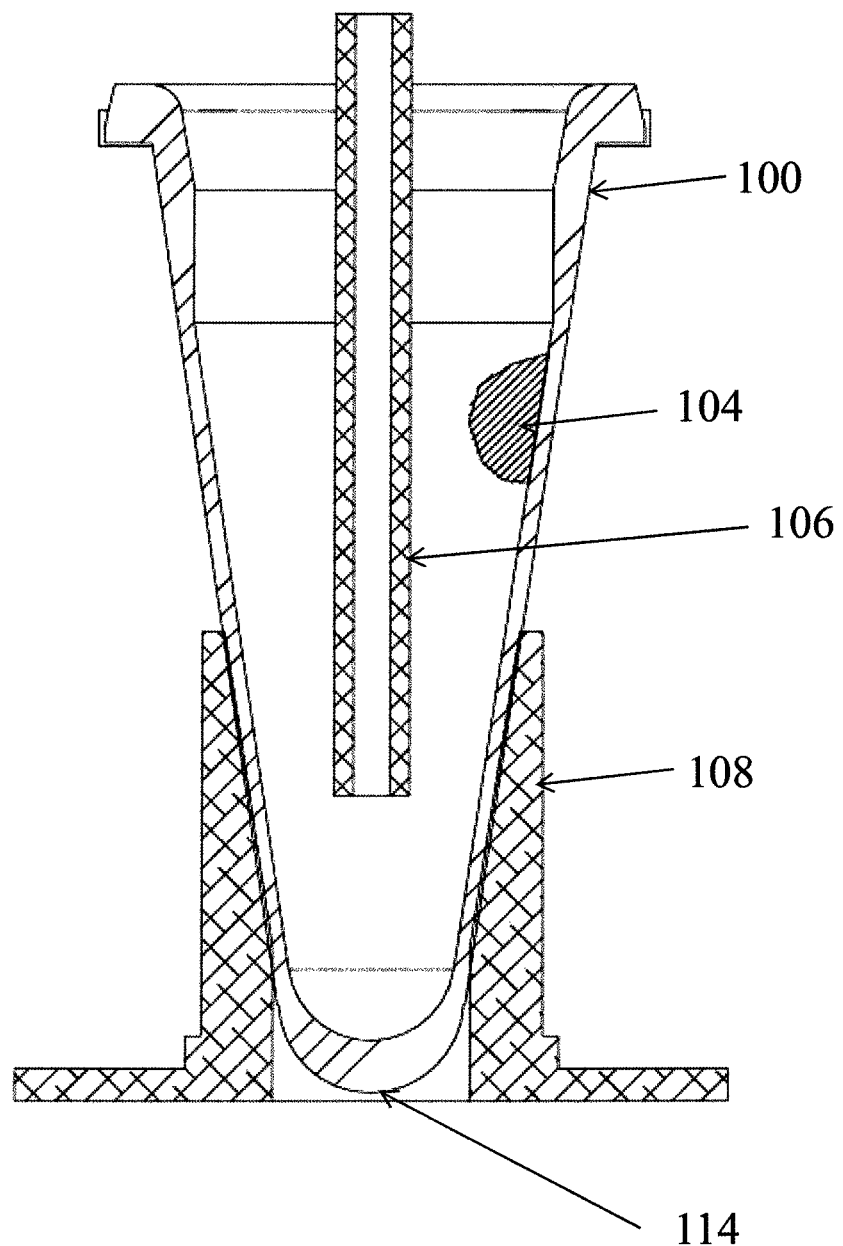

MICROFLUIDIC APPARATUS, METHOD, AND APPLICATIONS

RELATED APPLICATION DATA

The instant application claims priority to U.S. Provisional application Ser. No. 61/561,007 filed on Nov. 17, 2011, the subject matter of which is incorporated by reference herein in its entirety.

BACKGROUND

1. Field of the Invention

Embodiments of the invention are directed to the field of biology. More particularly, embodiments of the invention are directed to a system for use in processing formalin-fixed paraffin-embedded (FFPE) tissue samples for molecular biology studies, and applications thereof.

2. Description of Related Art

An aspect of histology relies on preserving tissue from decay for later examination or research. Such tissues are often preserved by subjecting them to a chemical (often a formalin solution) that prevents decay both from autolysis and/or putrefaction of the tissue. Chemical fixatives may also preserve the tissue's structure by introducing chemical cross-linking among the amine groups of the tissue's proteins. The same tissues are then often embedded in a hydrocarbon matrix (often paraffin wax) to more conveniently store them in a solid phase and to more reliably remove thin slices of the fixed tissue for microscopic investigation. The tissues thus preserved are commonly termed formalin fixed paraffin embedded (FFPE). With the introduction of molecular biology, the FFPE tissues are not only destined for microscopic analysis but they may often be of interest for investigation of the genetic material also preserved in the tissue. In such cases the paraffin wax needs to be removed from the tissue and the cross-linking resulting from the fixative needs to be reversed in order to separate the genetic material from the FFPE tissue and render it compatible with the chemistry required for molecular biology investigation of the tissue. FFPE tissue samples are traditionally dewaxed from the paraffin wax by placing the embedded tissue sample in a xylene solution. The paraffin wax then dissolves into the xylene, whereafter the tissue sample is removed from the xylene and rehydrated with an ethanol/xylene mixture in series dilution processes. Alternatively, xylene may be sprayed onto a tissue sample and the dissolved paraffin "washes away" as new xylene is applied to the tissue sample. While xylene is an efficient solvent for sample de-waxing, its introduction into tissue processing steps makes the chemistry used in molecular biology difficult; it is also a hazardous chemical for lab technicians to handle (generally requiring a ventilated hood and special waste disposal means), and its organic nature makes many aqueous buffer steps automation a challenge. A system that can accomplish the removal of the paraffin wax without the use of xylene is advantageous. Furthermore, if the system were an aqueous system compatible with subsequent molecular biology processes for nucleic acid assays, the technique would be a significant improvement over the use of xylene.

Tissue samples embedded in paraffin wax are often "fixed" chemically prior to embedding. The fixing is accomplished by formation of cross-linking methylene bridges between amino groups. This polymeric network structure results in low permeability of macromolecules in a protein's backbone but the structural features of the protein molecules are well preserved. The chemical cross-linking renders the tissue immune from decay. Therefore it can then be stored for long periods in ambient conditions. In order for the fixed tissue to yield nucleic acids suitable for molecular biological investigation the chemically induced cross-linking needs to be reversed so that the nucleic acids can be purified out of the tissue sample. The de-cross-linking can be achieved through subjecting the tissue sample (once the paraffin has been removed) to a suitable buffer which may also contain a detergent or a surfactant and suitably elevated temperatures to reverse the cross-linking. Therefore a system and method that can easily remove the paraffin wax from the tissue and then proceed to de-crosslink the macromolecules thus rendering the tissue sample in a condition compatible with classical aqueous based sample preparation, purification and nucleic acid amplification would be very useful and, even more advantageous if the system can be performed automatically.

SUMMARY

An embodiment of the invention described herein is a liquid-liquid extraction system that is compatible with standard laboratory materials and techniques. It is also compatible with many established automation procedures used to perform nucleic acid extraction. The dewaxing occurs when the FFPE sample that is contained in an aqueous buffer solution is heated above the melting point of the paraffin. The aqueous solution is covered with an immiscible liquid such as silicon oil or some other oil that is less dense than the aqueous solution and with a boiling point higher than the boiling point of the aqueous solution. In such case, since the paraffin is immiscible with the aqueous solution and it is also less dense than the aqueous solution, the melted paraffin floats to the surface of the aqueous solution and enters the oil phase in which it is miscible and thereby it is permanently separated from the aqueous solution in which the tissue sample resides.

An embodiment of the invention is related to a method for purifying nucleic acids from FFPE tissue samples in aqueous buffer. The method comprises a liquid-liquid extraction in a reaction vessel, a layer of oil that is a lower density than the aqueous buffer floats on top of a bottom layer aqueous solution containing the FFPE tissue sample. The FFPE tissue sample to be processed is placed and resides in the aqueous solution during the entire process. The aqueous solution is heated above the melting point of the paraffin wax in the tissue sample and since the paraffin wax is a lower density than the aqueous solution, the melted paraffin wax floats to the surface of the aqueous solution and in contact with the oil floating on the surface. Since the paraffin is miscible with the oil it mixes into the oil and thereby becomes permanently separated from the aqueous solution and the tissue sample. The tissue sample remains in the aqueous phase in the reaction vessel where it is available for further processing such as de-crosslinking, cell lysis, and nucleic acid purification so that the genetic materials of the tissue sample is ready for further analysis. The composition for use in an extraction reaction vessel (hereinafter referred to as a "tube") may be a solid in the tube at room temperature and under expected storage temperatures and conditions, and which becomes a liquid that covers a solution's exposed surface in the tube upon a first rise in temperature during an extraction reaction. Alternatively, an oil such as silicone oil can be added to the tube either before, during or after the tissue sample and the aqueous buffer are added wherein the oil being of a lower density than the aqueous solution separates from the aqueous solution and floats on the surface of the aqueous solution containing the tissue sample.

An embodiment of the invention is a composition as mentioned immediately above, in the form of a controlled mixture of high purity silicone oil and wax. Again, the mixture is a solid at typical room temperatures and under expected storage conditions (temperature, etc.). The mixture is disposed as a layer of solid material on the inside surface of an extraction tube below the opening of the tube; with or without a tissue sample being present in the tube. When the temperature is raised above the melting point of the silicone oil wax mixture after the tissue and an aqueous solution is introduced into the tube, the mixture melts and covers the surface of the solution. Alternatively, an oil such as high purity silicone oil is added to the tube either before, during or after the tissue sample and aqueous solution are added to the tube. In either case the floating immiscible layer prevents evaporation of the aqueous solution during the extended heating period. The process leaves the tissue sample free of paraffin wax and in the aqueous phase of the solution in the tube. In the case where the tissue was "fixed" prior to becoming embedded in paraffin wax, the aqueous solution that contains the tissue in the tube can be a mixture of a chaotropic buffer and a surfactant. The tissue sample in the chaotropic buffer and surfactant mixture upon dewaxing will also be de-crosslinked by the action of the chaotropic buffer and surfactant mixture at an elevated temperature during which the chemical linkages formed by the chemical fixing agent in the tissue's protein network are hydrated. Meanwhile, the oil or silicone oil wax mixture (now with the added paraffin wax from the tissue sample) continues to act as an evaporation barrier for the solution. Upon completion of the dewaxing and the extraction, the tissue sample containing nucleic acid may be lysed and the lysate removed from underneath the oil layer seal by inserting a tube, lumen, or pipette into the solution and extracting the solution through the tube, lumen, or pipette. According to an aspect, the mixture consists of wax=1% to 20% by volume and the balance silicone oil. According to an aspect, the mixture consists of approximately 5% wax and 95% silicone oil. The wax may be standard PCR wax (e.g., Sigma Aldrich paraffin wax having a melting point of 58° C.-62° C.). Alternatively any high purity paraffin wax ($C_{20}H_{42}$—$C_{40}H_{82}$) with melting points between 46° C.-68° C.) may be used. Alternatively, the liquid oil may be any high purity silicone oil or a high purity hydrocarbon such as mineral oil.

An embodiment of the invention is a method for reducing or preventing evaporation of a solution in an extraction reaction tube while at the same time providing a selective phase for the paraffin that melts out of a tissue sample to mix and separate from the aqueous phase of the extraction reaction. The method includes the steps of coating at least a portion of the inner wall of the reaction tube with a controlled mixture of silicone and wax, in solid form, prior to an extraction reaction. Alternatively, the method includes the step of adding a liquid oil prior to, during, or after adding the tissue sample and an aqueous phase buffer to the tube. The reaction involves heating the tube and creating a condition that transforms the solid mixture into a (immiscible) liquid that floats on the surface of a solution in the tube and thereby seals the tube to prevent evaporation and, provides a liquid phase for the paraffin melted out of a tissue sample to mix into. Alternatively, the liquid oil floats to the top of the aqueous solution and while the solution is heated the oil seals the tube to prevent evaporation and provides a liquid phase for the paraffin melted out of a tissue sample to mix into. In an aspect, the condition that transforms the solid mixture into a liquid is (but is not limited to) a heating process. In an aspect, the method involves coating at least a portion of the inner wall of the tube with mixture of 1% to 20% by volume wax and the balance silicone oil. In an aspect, the method involves using a mixture of approximately 5% wax and 95% silicone oil. In an aspect, the method further involves using liquid-liquid extraction method in which an aqueous layer's surface is covered by a layer of an immiscible oil liquid mixture of lower density.

An exemplary embodiment of the invention is a method for nucleic acid purification. The method involves the steps of: providing a formalin-fixed paraffin-embedded (FFPE) tissue sample in an aqueous solution having a density and a boiling point, in a vessel; providing an immiscible liquid or a precursor phase thereof, having a density that is less than the density of the aqueous solution and a boiling point that is greater than the boiling point of the aqueous solution, in the vessel; and performing a liquid-liquid extraction to remove the paraffin from the tissue sample prior to a nucleic acid purification step. In various non-limiting exemplary and illustrative aspects, the embodied invention may include the following features and/or characteristics:

further comprising performing the liquid-liquid extraction step and the nucleic acid purification step in a single microfluidic device;

further comprising providing a silicon oil as the immiscible liquid;

further comprising providing a mineral oil as the immiscible liquid;

further comprising providing a solid silicone oil/wax mixture as the immiscible liquid or a precursor phase thereof;

wherein the liquid-liquid extraction step further comprises raising the temperature of the aqueous solution in the vessel above the melting point of the paraffin embedding the tissue sample;

where the solution is a mixture of a chaotropic buffer and a surfactant;

further comprising adding a protein digesting enzyme to the solution following the removal of the paraffin from the tissue sample.

An exemplary embodiment of the invention is a microfluidic device. The device includes at least one dedicated liquid-liquid extraction process vessel; a nucleic acid purification process component fluidically coupled to the vessel via a first microfluidic channel; and at least one nucleic acid amplification reactor fluidically coupled to the nucleic acid purification process component via at least a second microfluidic channel that is different than the first microfluidic channel, wherein there is no direct microfluidic connection between the at least one dedicated liquid-liquid extraction process vessel and the at least one nucleic acid amplification reactor.

An exemplary embodiment of the invention is a liquid-liquid extraction and nucleic acid purification kit. The kit includes a microfluidic device capable of performing both a liquid-liquid extraction process and a nucleic acid purification process, including at least one dedicated liquid-liquid extraction process vessel, an immiscible liquid or a precursor phase thereof disposed in the at least one vessel, a nucleic acid purification process component fluidically coupled to the vessel, and at least one nucleic acid amplification reactor fluidically coupled to the nucleic acid purification process component; and a supply of reagents suitable to enable the liquid-liquid extraction process and the nucleic acid purification process.

All embodiments and aspects of the invention are particularly applicable to microfluidic systems, methods, and applications.

BRIEF DESCRIPTION OF THE DRAWINGS

FIG. 1B is a cross sectional view of a tube showing a solid wax/silicone mixture disposed on an upper portion of the inner surface of the tube, inserted into an associated tube heater prior to introducing a fluid and prior to introducing a FFPE tissue sample into the tube and prior to heating the tube. The tube also includes a lumen for introduction of fluid into the tube and for extraction of fluid from underneath the wax/silicone layer after the reaction is complete, according to an illustrative embodiment of the invention;

FIG. 2B shows a layer of oil disposed on the surface of the liquid having been added to the tube either before, during, or after the aqueous liquid containing a FFPE tissue sample was added to the tube. In an exemplary aspect, high purity silicone oil is disposed into a tube preloaded with an aqueous solution containing an FFPE tissue sample, the tube is heated to an elevated temperature for melting the wax in the tissue sample, which floats into the silicone oil. The tube also includes a lumen for introduction of fluid and/or liquid oil into the tube and for extraction of fluid from underneath the wax/silicone layer after the reaction is complete, according to an illustrative embodiment of the invention;

DETAILED DESCRIPTION OF NON-LIMITING, EXEMPLARY EMBODIMENTS OF THE INVENTION

Figure 1A:
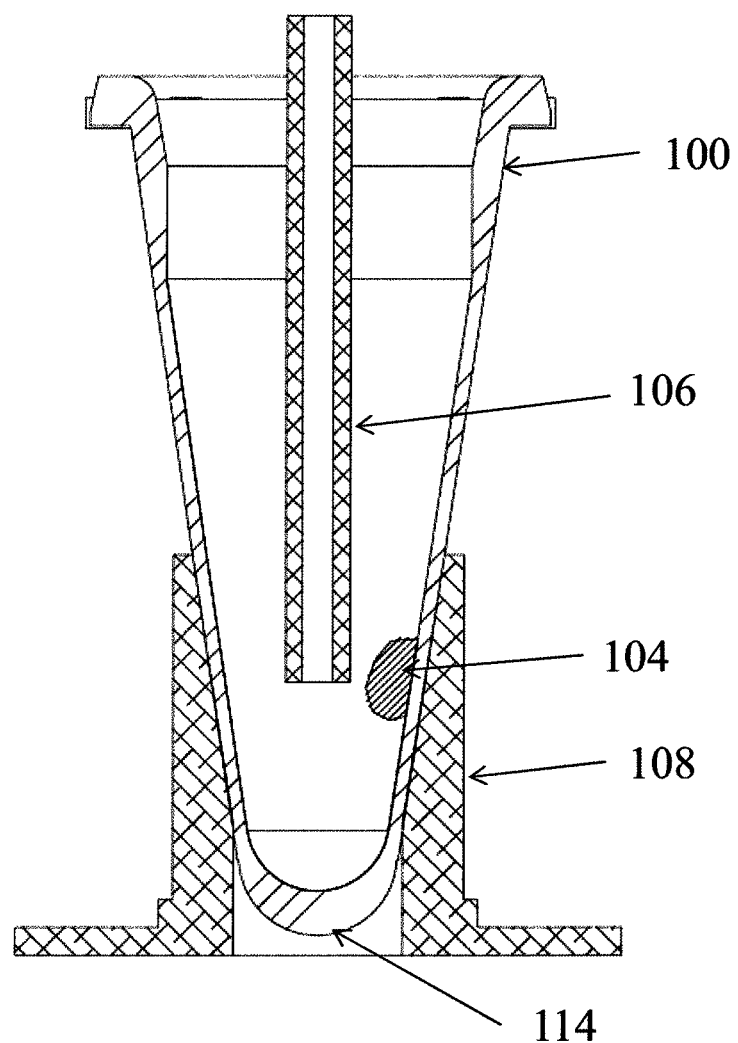
FIG. 1A is a cross sectional view of a vessel used exclusively for a liquid-liquid extraction process (hereinafter referred to as a ('tube'), showing a solid wax/silicone mixture disposed on a lower portion of the inner surface of the tube, inserted into an associated tube heater prior to introducing a fluid and prior to introducing a FFPE tissue sample into the tube and prior to heating the tube. The tube also includes a lumen for introduction of fluid into the tube and for extraction of fluid from underneath the wax/silicone layer after the reaction is complete, according to an illustrative embodiment of the invention.
Figure 1C:
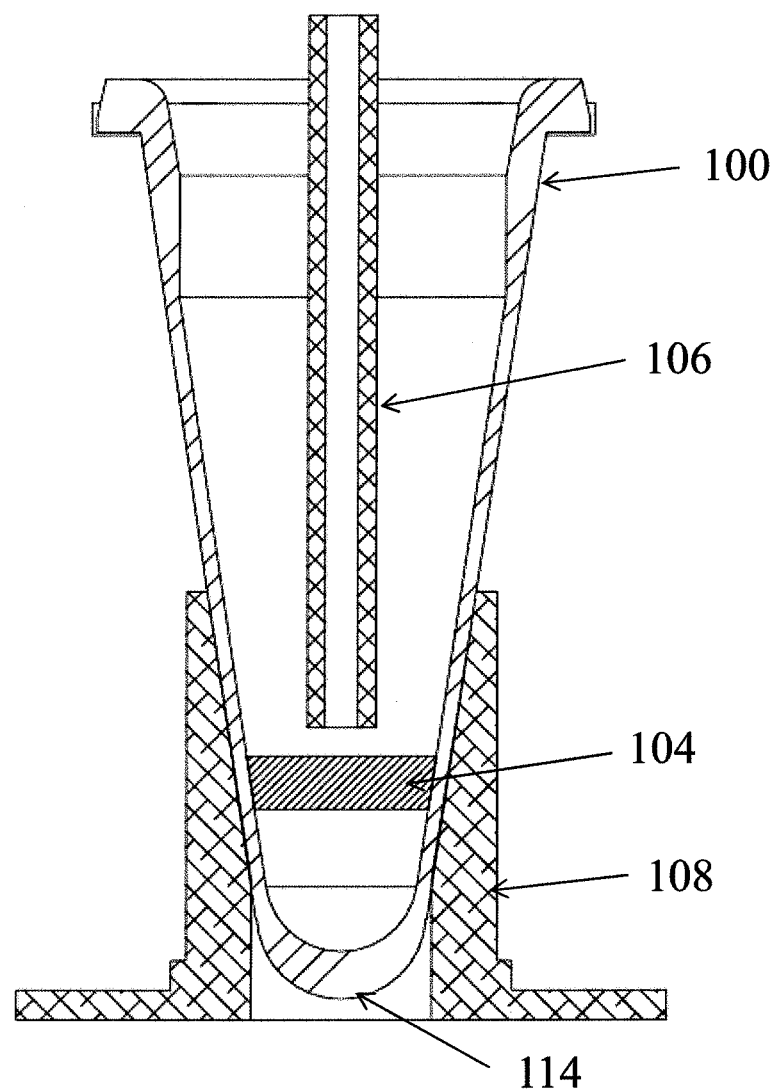
FIG. 1C is a cross sectional view of an alternative arrangement of a tube showing a solid wax/silicone mixture disposed as a ring on a portion of the inner surface of the tube, inserted into an associated tube heater prior to introducing a fluid and prior to introducing a FFPE tissue sample into the tube and prior to heating the tube. The tube also includes a lumen for introduction of fluid into the tube and for extraction of fluid from underneath the wax/silicone layer after the reaction is complete, according to an illustrative embodiment of the invention.

As shown in FIGS. 1A-1C, a tube (dedicated liquid-liquid extraction process vessel) 100 is in the form of a cone-shaped ampule that tapers to a closed, bottom end 114. The tube may include a silicone oil (95%)/wax (5%) mixture 104 either placed low (towards the bottom) on the inside surface of the tube as in FIG. 1A, or high (towards the top) on the inside surface of the tube as in FIG. 1B, or as a ring coating a portion of the inside surface of the tube (either low or high) as shown in FIG. 1C.

Figure 2A:
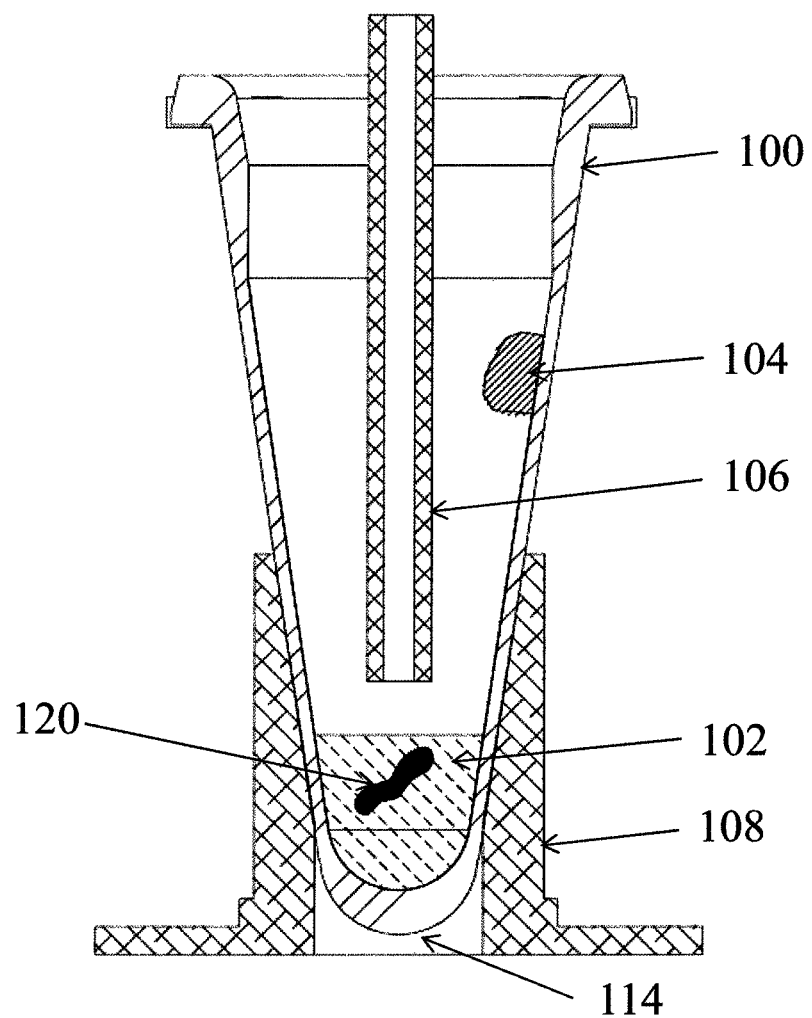
FIG. 2A is a cross sectional view of a tube showing a solid wax/silicone mixture disposed on an upper portion of the inner surface of the tube, inserted into an associated tube heater after introducing a fluid and a FFPE tissue sample into the tube and prior to heating the tube. The tube also includes a lumen for introduction of fluid into the tube and for extraction of fluid from underneath the wax/silicone layer after the reaction is complete, according to an illustrative embodiment of the invention.

As shown in FIG. 2A, a FFPE tissue sample 120 and an aqueous solution (hereinafter, the "solution") 102 are introduced into the tube and subjected to heating by associated tube heater 108. During the process, the small volume of solution 102 in the tube is subject to evaporation due to the elevated temperatures. The evaporation can be circumvented by installing a tightly sealed cap clamped under a pressurized lid at the top of the tube to prevent the cap from becoming loose; however, this type of cap arrangement will not meet the requirements of an automated workflow system design since an automated workflow needs the ability to access the fluid in the tube. Therefore, according to the invention, the silicone oil (95%)/wax (5%) mixture 104 is designed to melt upon heating of the tube and cover the surface of the solution; or, a high purity silicone oil or another high purity mineral oil may be provided to cover the surface of the solution to prevent evaporation, in place of a capping system. The silicone oil (95%)/wax (5%) mixture 104 or the high purity oil is selected as an advantageous extraction media for the paraffin that is melted out of the FFPE tissue sample during heating of the solution containing the FFPE tissue sample. The lumen 106 provides a fluidic pathway to and from the tube for transporting solutions to and from the tube and to and from other reservoirs (e.g., purification system 125, FIG. 3) of the system while also minimizing evaporation from the tube during the elevated temperature duration(s) of the process.

Figure 2B:
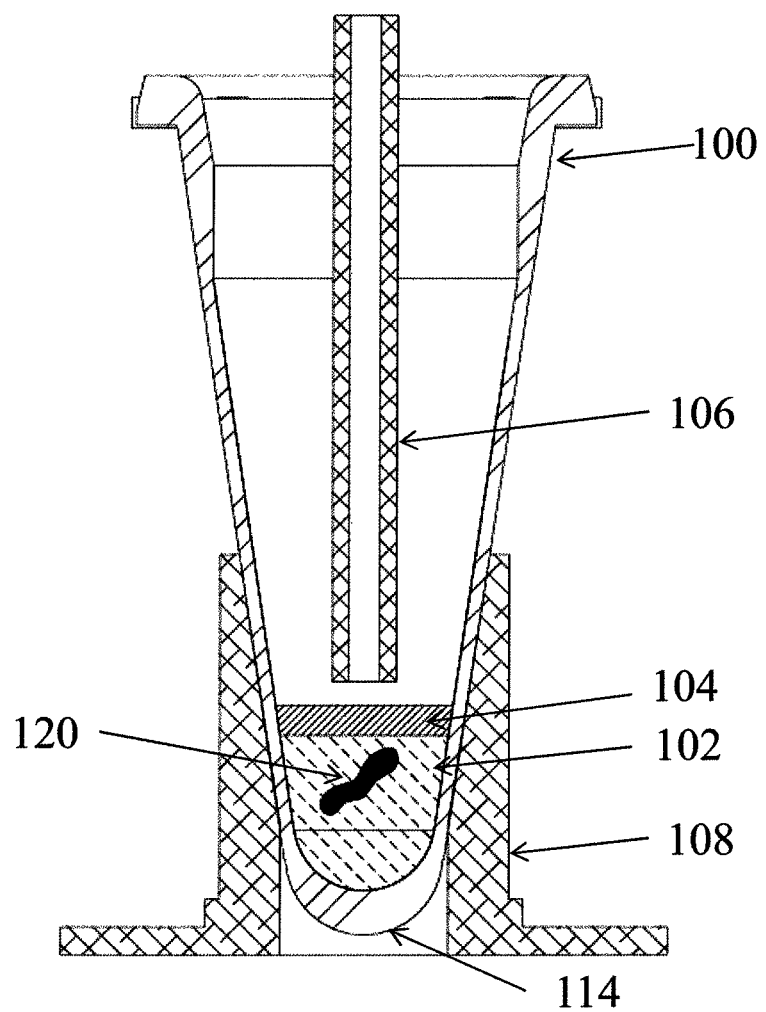
FIG. 2B is a cross sectional view of a tube showing a wax/silicone mixture disposed on the surface of the liquid in the tube, inserted into an associated tube heater and after heating the tube. Alternatively.

As shown in FIG. 2B, a layer of an immiscible liquid, e.g., a silicone oil (95%)/wax (5%) mixture 104 floats on the surface of the solution 102 and can efficiently prevent the solution from evaporating while, at the same time forms a layer for selectively extracting paraffin wax out of the solution after the paraffin melts out of the FFPE tissue sample. Alternatively, a high purity liquid oil may be dispensed into the tube after the FFPE tissue sample's introduction. The tube and its contents including the FFPE tissue sample, aqueous solution, and oil or wax/oil mixture are heated. The paraffin melts out of the FFPE tissue sample and, since it is immiscible in the aqueous phase and has a lower density than the density of the aqueous phase, migrates into the oil or wax/oil mixture floating on the surface of the aqueous phase and is thereby extracted and permanently separated from the aqueous phase. The immiscible, liquefied wax/silicone mixture, upon re-solidifying, will be at the height of the solution's surface when the tube is cooled. The tube is penetrated by a lumen 106 or a pipette tip for filling the tube with solution or in some cases the oil, and removing the reacted solution from underneath the oil or silicone oil/wax layer upon completion of the extraction.

Figure 2C:
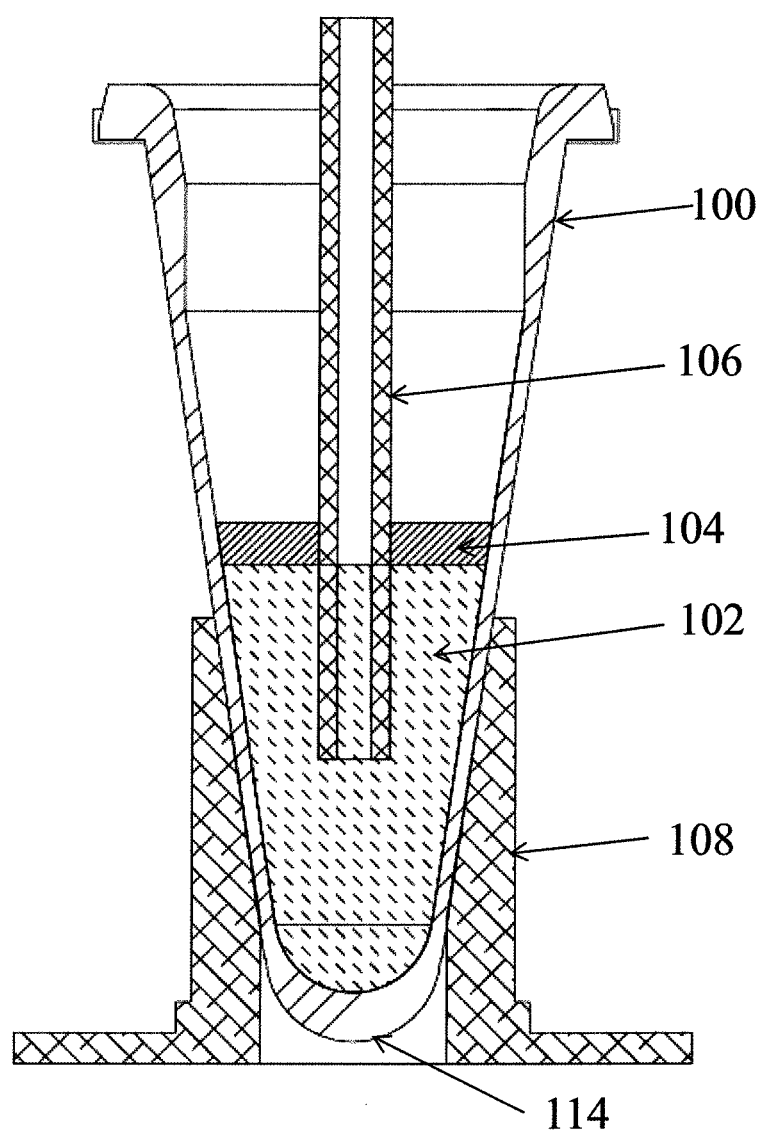
FIG. 2C is a cross sectional view of a tube inserted into an associated tube heater showing a lumen and showing the layer of a wax/silicon mixture after another volume of an aqueous buffer has been added to the tube. The added aqueous solution increases the volume above the bottom of the lumen to facilitate removal of a fraction of the aqueous solution from below the wax/silicone layer. The added volume may be the same aqueous solution originally dispensed into the tube, or another aqueous solution, and in either case the aqueous solution may include lysing reagents, detergents, surfactants, protein digesting enzymes, or other reagents known in the art and used to prepare a sample for nucleic acid purification, according to an illustrative embodiment of the invention.

As shown in relation to FIG. 2C, after the liquid-liquid extraction process is complete, aqueous phase reagents are additionally added to the tube. The reagents may include the same or a different solution than in the first volume of solution, lysing reagents, detergents, surfactants, protein digesting enzymes, or other reagents known in the art and used to prepare a biological sample for nucleic acid purification. The added aqueous solution increases the volume above the bottom of the lumen 106 to facilitate removal of a fraction of the aqueous solution from below the wax-oil layer 104.

Figure 2D:
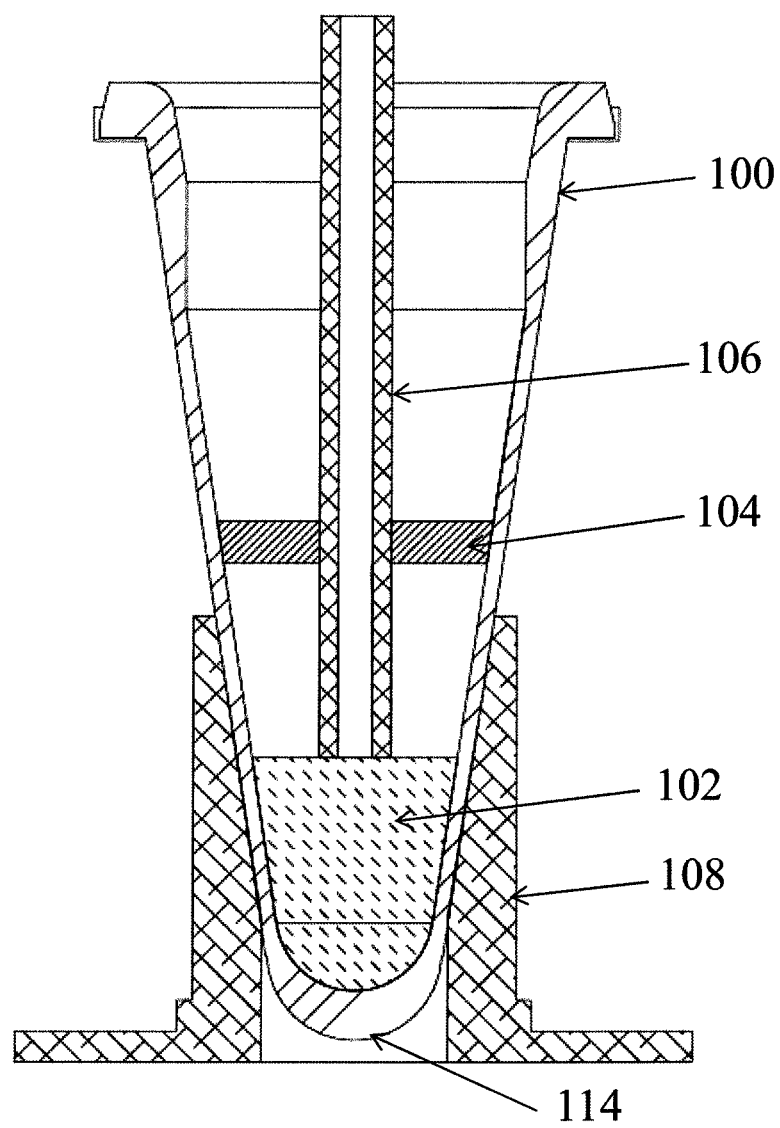
FIG. 2D is a cross sectional view of a tube inserted into an associated tube heater showing a lumen and showing a solidified layer of a wax/silicone mixture after a fraction of the liquid volume has been removed from the tube, according to an illustrative embodiment of the invention.
Figure 2E:
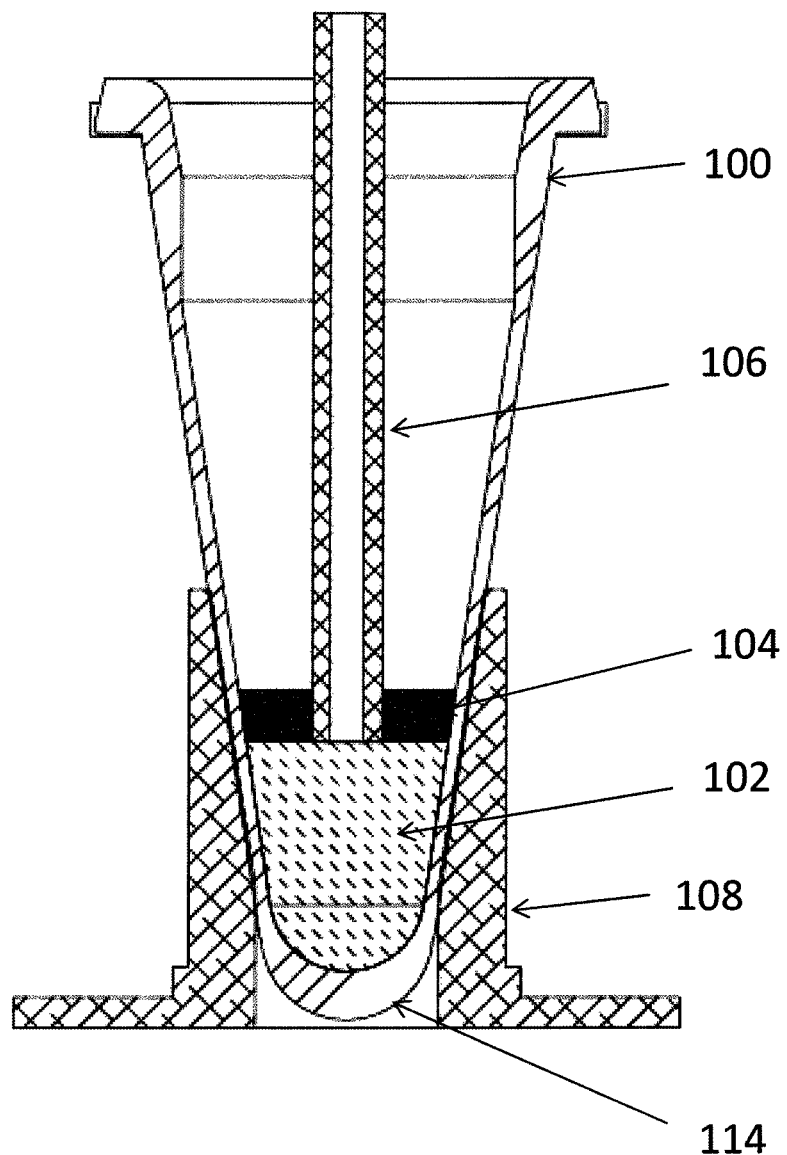
FIG. 2E is a cross sectional view of a tube inserted into an associated tube heater showing a lumen and showing a wax/oil layer in liquid form after the extraction and after the additional solution is first added and then removed from the tube via the lumen, according to an illustrative embodiment of the invention.

As shown in FIG. 2D, the added oil and all of the extracted wax from the FFPE sample may become a solidified wax/silicone layer 104 at lower temperatures or, the layer may remain liquid (which is depicted in FIG. 2E following the removal of a fraction of the aqueous phase) but in either case it remains in the tube after a fraction of solution 102 is removed.

Figure 3:
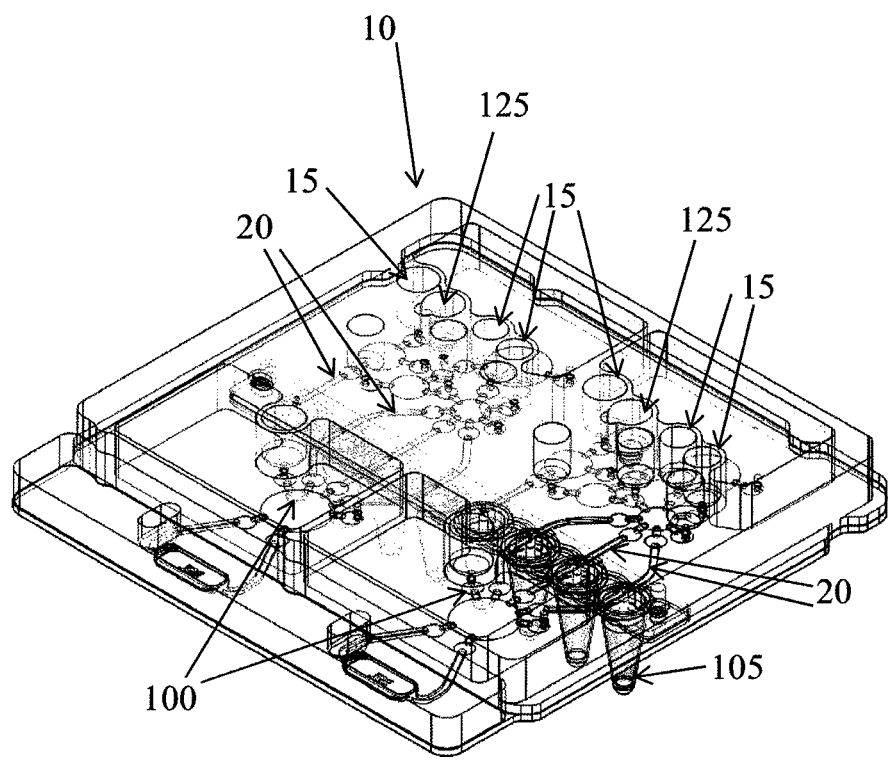
FIG. 3 is a perspective view of a microfluidic device for use in an automated microfluidic system showing two side-by-side liquid-liquid extraction and nucleic acid purification systems. Each of the two systems include at least one tube for carrying out a liquid-liquid extraction process on a FFPE tissue sample to remove the paraffin embedding the tissue sample and prepare the tissue for classical automated purification of the nucleic acids used to analyze the tissue sample in a nucleic acid purification component of the system coupled to the tube via a microfluidic channel, according to an illustrative embodiment of the invention.
Figure 4:
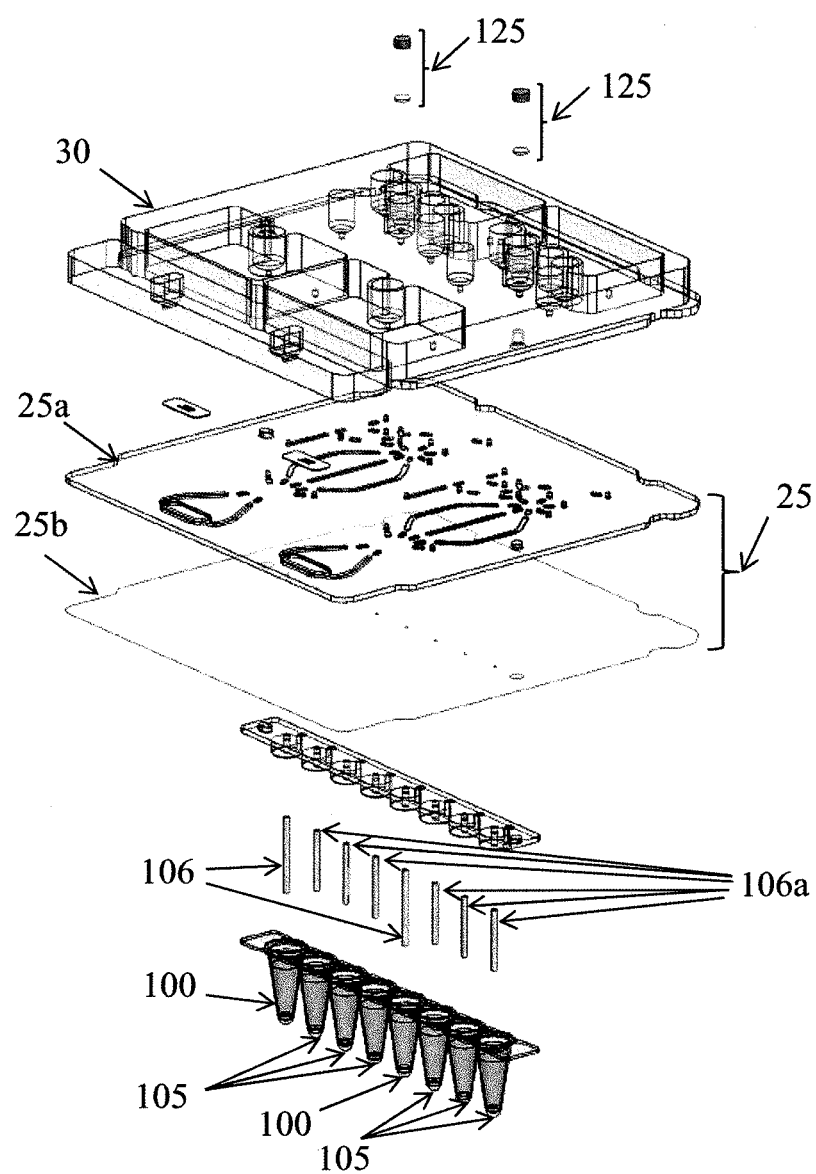
FIG. 4 is an exploded view of the exemplary microfluidic device shown in FIG. 3, according to an illustrative embodiment of the invention.
Figure 5:
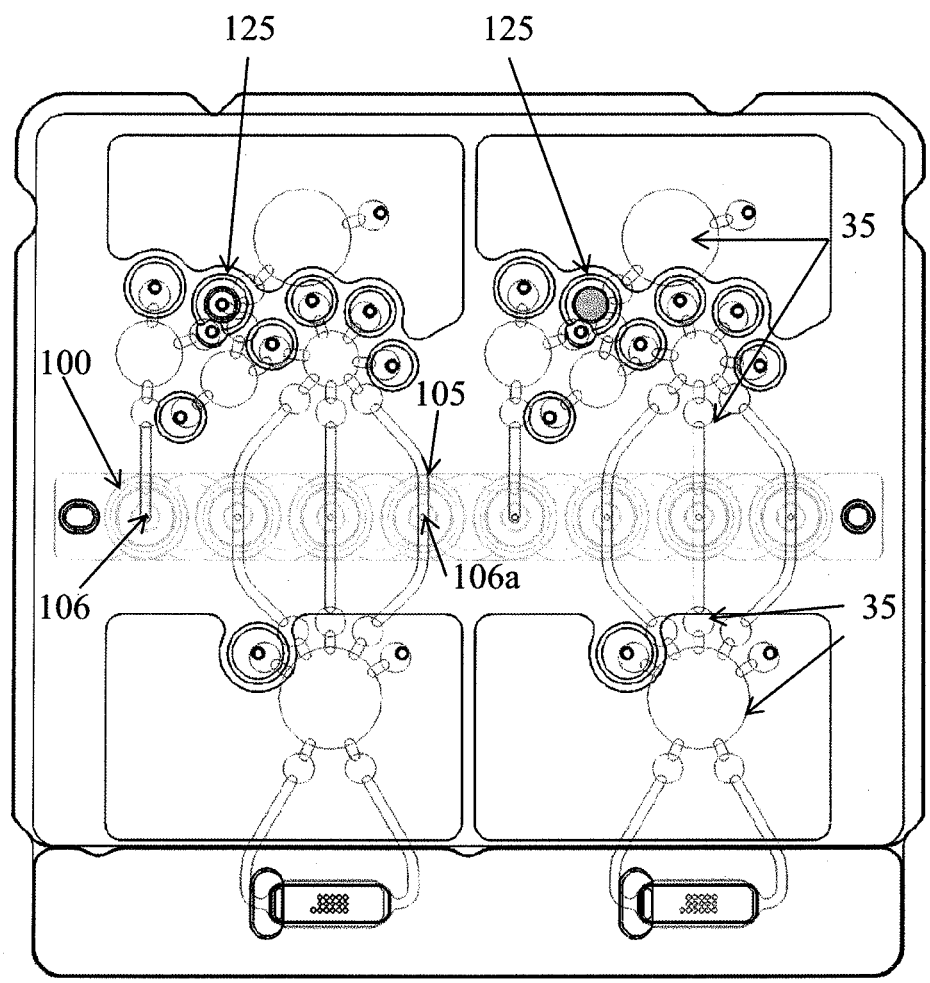
FIG. 5 is a plan view of a the exemplary microfluidic device shown in FIG. 3, according to an illustrative embodiment of the invention.

FIGS. 3, 4, and 5 show various views of an exemplary microfluidic device 10 (e.g., Rheonix CARD Consumable) that can be employed in an automated microfluidic system (e.g., Rheonix Encompass platform). Further information is provided in US 2012/0045799 and US 2012/0129714, the subject matters of which are herein incorporated by reference in their entireties to the fullest extent allowed by applicable laws and rules. A plan view of an illustrative dual system (side-by-side/top-bottom) microfluidic device is shown schematically in FIG. 5. Referring to the 'top-half' system in FIG. 5 and to the exploded view in FIG. 4, the device 10 includes at least one tube (dedicated liquid-liquid extraction process vessel) 100 and associated lumen 106, at least one nucleic acid amplification reactor 105 and associated lumen 106a, at least one heater 108 associated with each tube disposed to heat the at least one tube and the least one nucleic acid amplification reactor, and a nucleic acid purification system 125 fluidically coupled to the at least one tube 100 by a microfluidic channel 20a and to the at least one reactor 105 by a different microfluidic channel 20b. Although the microfluidic device 10 also shows a microarray chamber and a nucleic acid analyzer component on the left-hand side of FIG. 5, it will be appreciated that analysis can be performed in the one or more amplification reactors. It should also be noted that there is no direct microfluidic connection between the at least one tube 100 and the least one nucleic acid amplification reactor 105. This device 10 is capable of performing both a liquid-liquid extraction process and a nucleic acid purification process. Device 10 may also form the basis of an automated liquid-liquid extraction and nucleic acid purification kit, which further includes a supply of reagents suitable to enable the liquid-liquid extraction process and the nucleic acid purification process, as described herein.

FIG. 3 more particularly schematically illustrates a dual system microfluidic device 10 that incorporates in each system a single tube 100, three amplification reactor tubes 105, reservoirs 15, purifiers 125, and microfluidic channels 20a, 20b, which can be utilized to complete a fully integrated molecular assay from a FFPE sample to microarray analysis of the gene amplification products.

As shown in FIG. 4, the microfluidic system 10 is assembled from a two-layer microfluidic channel system 25 made up of a channel layer 25a and film layer 25b with an attached reservoir layer 30 (the reservoir layer 30 and the channel layer 25a may be formed from the same substrate though, for clarity, they are shown as separate). A channel network is composed of the film layer 25b selectively bonded to channel layer 25a. The channels 20 are first prepared by creating a series of disconnected elongated depressions (open channels) in the face of the substrate of channel layer 25a facing film layer 25b. The channels 20 are then enclosed by selectively bonding the film layer while at the same time creating diaphragms 35 that, when actuated using instrument interface 50 (FIG. 6), provide a means for the channels 20 to communicate, and with coordinated actuation of the diaphragms 35 fluids can be pumped from one location in the system 10 to other locations for the purpose of completing an assay. Penetrating the film layer 25b and accessed by channels 20 are lumens 106 and 106a. Attached to the film layer, tube 100 is accessed by lumen 106 while lumens 106a access amplification reactors 105. Present in the reservoir layer is one or more purifiers 125, which may be composed of any known material capable of selectively binding nucleic acids in order to separate the nucleic acids from cell lysate. The purifier 125 may be composed of a silica matrix. In an alternative arrangement, the silica matrix may be composed of silica beads.

As further shown in FIG. 5, tube 100 is accessed by lumen 106 that is incorporated into a separate channel network (20a) than the channel network (20b) for amplification reactors 105, which are accessed by lumens 106a. As described above, the FFPE tissue sample is first placed into tube 100 and then the tube strip containing tube 100 and amplification reactors 105 are assembled onto the microfluidic system 10. Thereafter the reagents required for the liquid-liquid extraction are provided, the liquid-liquid extraction is accomplished, and then certain reagents are added to the tube though lumen 106 to proceed through the chemical de-cros slinking and lysing of the sample; thereafter a fraction of the processed solution is withdrawn through lumen 106 and further purified to provide any nucleic acids that were withdrawn from the original liquid fraction using the other components of the system. The purified nucleic acids from the original tissue sample are then eluted from the purification system and delivered through lumens 106a to one or more amplification reactors 105 along with the required reagents to perform a nucleic acid amplification of selected sequences potentially included in the nucleic acids delivered to the amplification reactor from the original tissue sample.

Figure 6:
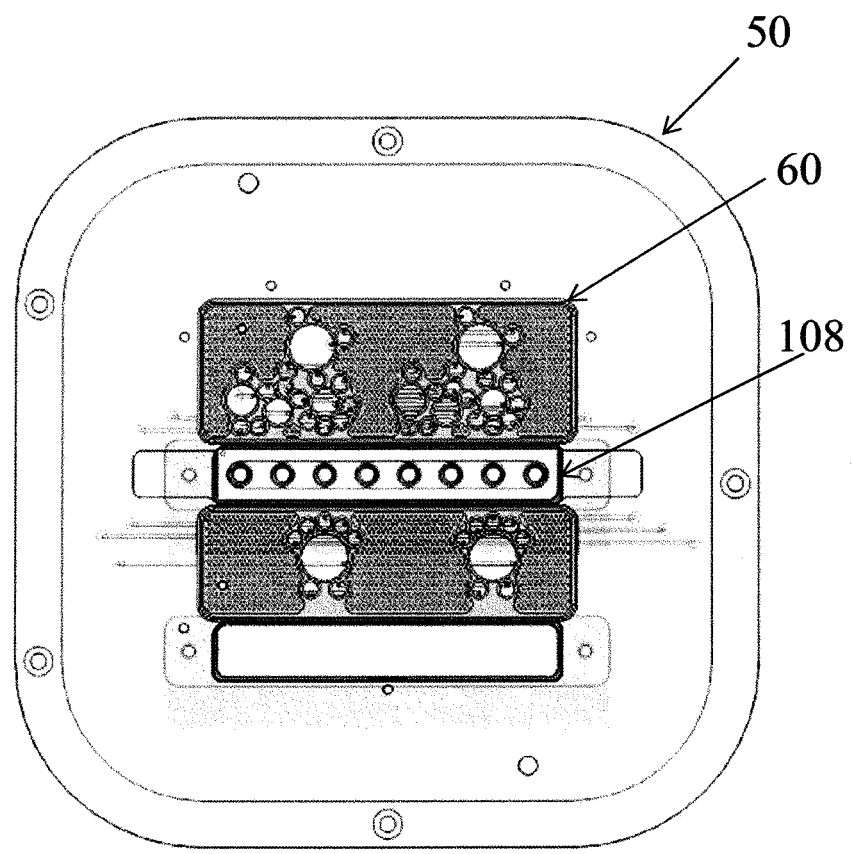
FIG. 6 is a plan view of an automated microfluidic system interface for the exemplary microfluidic device shown in FIG. 3, according to an illustrative embodiment of the invention.

FIG. 6 shows a plan view of the instrument interface 50 for a multiple reactor system that may be employed by an automated microfluidic system. Diaphragms 35 (FIG. 5) align with gasket layer 60 for pneumatic actuation of diaphragms 35 to pump fluids selectively through microfluidic system 10. At least two extraction reactors 100 seat into heater 108 (that may be a part of the same heater assembly as those used to heat the amplification reactors 105 or, heater 108 may be a separate heater assembly) to process the FFPE tissue samples to remove the paraffin embedding the tissue sample and prepare the tissue for automated purification of the nucleic acids from the cells in the tissue sample used to analyze the sample.

In each case described in FIGS. 1 to 6, the solution in the tube can be a mixture of a lysing buffer and a surfactant, among other reagents known in the art. The aqueous mixture, while at an elevated temperature, acts to de-crosslink the macromolecules in the tissue sample. Upon completion of the lysing and the de-crosslinking, a protein digesting enzyme may be added to the solution to further prepare the nucleic acids in the reacted solution for purification and later analysis. Alternatively, the tissue sample in the aqueous mixture may be lysed with the aid of protein digesting enzyme at elevated temperatures followed by incubation at higher temperatures for de-cross-linking.

Example 1

1. Place three 10 mg formalin fixed paraffin embedded (FFPE) tissue samples in a tube pre-coated with 10 µl of silicone oil/wax mixture droplet, or supply high purity oil prior to attaching the tube to the microfluidic system or through the lumen after attaching the tube to the microfluidic system;
2. Attach the tube to the microfluidic system;
3. Supply 15 µl Tween 20+15 µl of lysis buffer to the sample tube;
4. Heat and maintain the reaction temp at 95° C. for 10 min;
5. Lower the tube temp to 56° C.;
6. Supply 5 µl Tween 20+5 µl lysis+4 µl Proteinase K to the tube;
7. Maintain the reaction temp at 56° C. for 30 min;
8. Supply 15 µl EtOH to the tube;
9. Lower the tube temp to 35° C.;
10. Remove the sample solution from tube and direct it into microfluidic system's purifier 125 (FIG. 5; either a silica bead based or silica filter based system);
11. Remove the reaction solution to waste reservoir through the purifier;
12. Wash the purifier with 2×50 µl Wash buffer;
13. Re-wash the purifier with 2×50 µl Wash buffer;
14. Dispense 50 µl water into the purifier;
15. Remove the water to waste reservoir through the side channel in the purifier;
16. Repeat 14-15;
17. Remove the remaining water to waste reservoir through the purifier;
18. Dispense 20 µl elution solution into purifier;
19. Incubate for 30 sec;
20. Withdraw a fraction of the elution solution from the purifier and direct it into the amplification reactor;
21. Dispense an appropriate amplification master mix to the amplifier (the elution may be mixed with the master mix prior to filling the amplification reactor;
22. Amplify the elution;
23. Analyze the amplicons.

Figure 7:
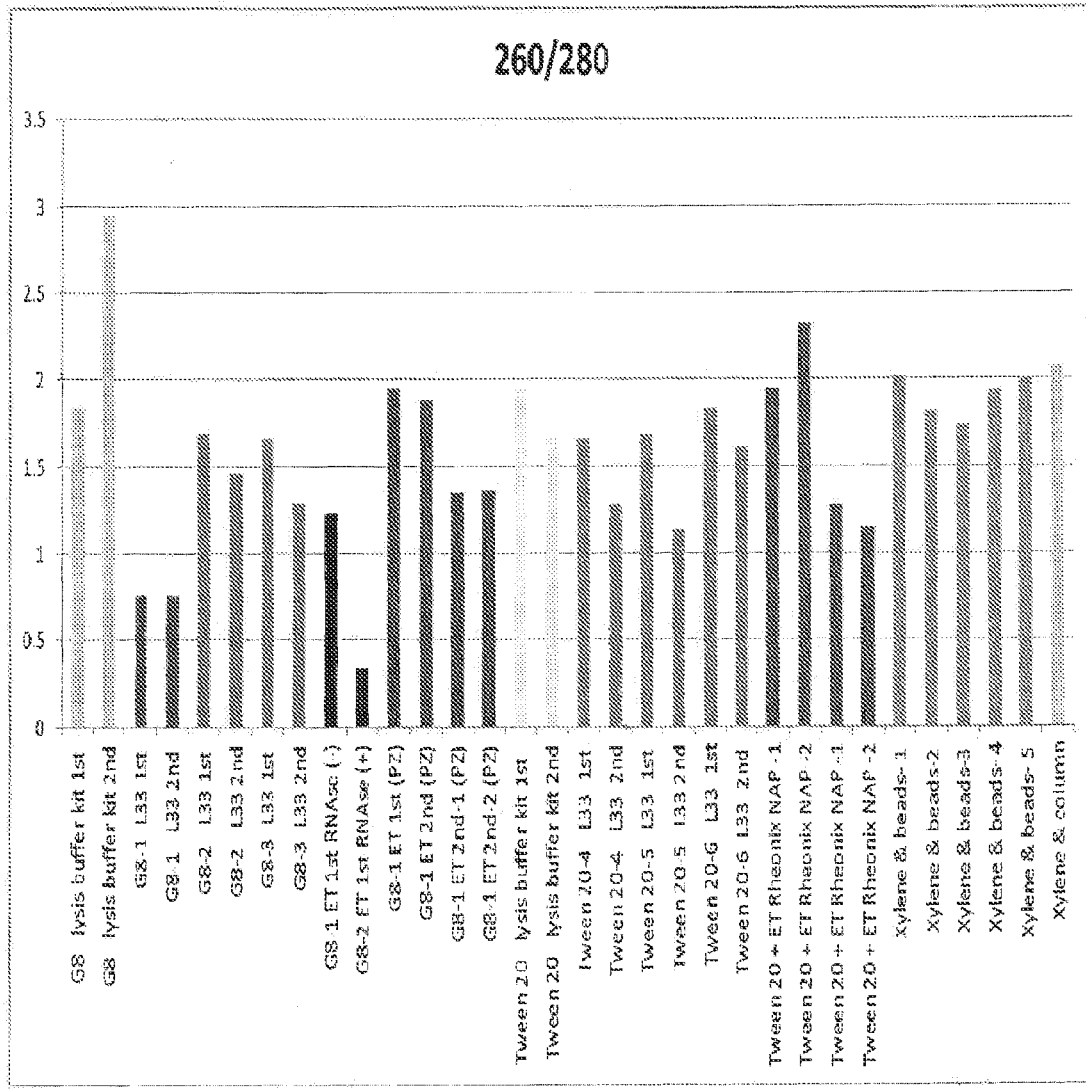
FIG. 7 shows qualitative results from subjecting eluted DNA recovered from the embodied system/method to analytical ultraviolet light ($\lambda$=260 nm; $\lambda$=280 nm), according to an illustrative embodiment of the invention.

FIG. 7 shows the resulting purity of DNA recovered using a microfluidic system that performs the liquid-liquid extraction followed by de-crosslinking, lysing and traditional silica based affinity capture of nucleic acids with later elution. The purity estimate is accomplished using the traditional A260/A280 method of UV measurement. The results compare the liquid-liquid extraction system using various buffers and surfactants to the traditional xylene extraction method.

Figure 8:
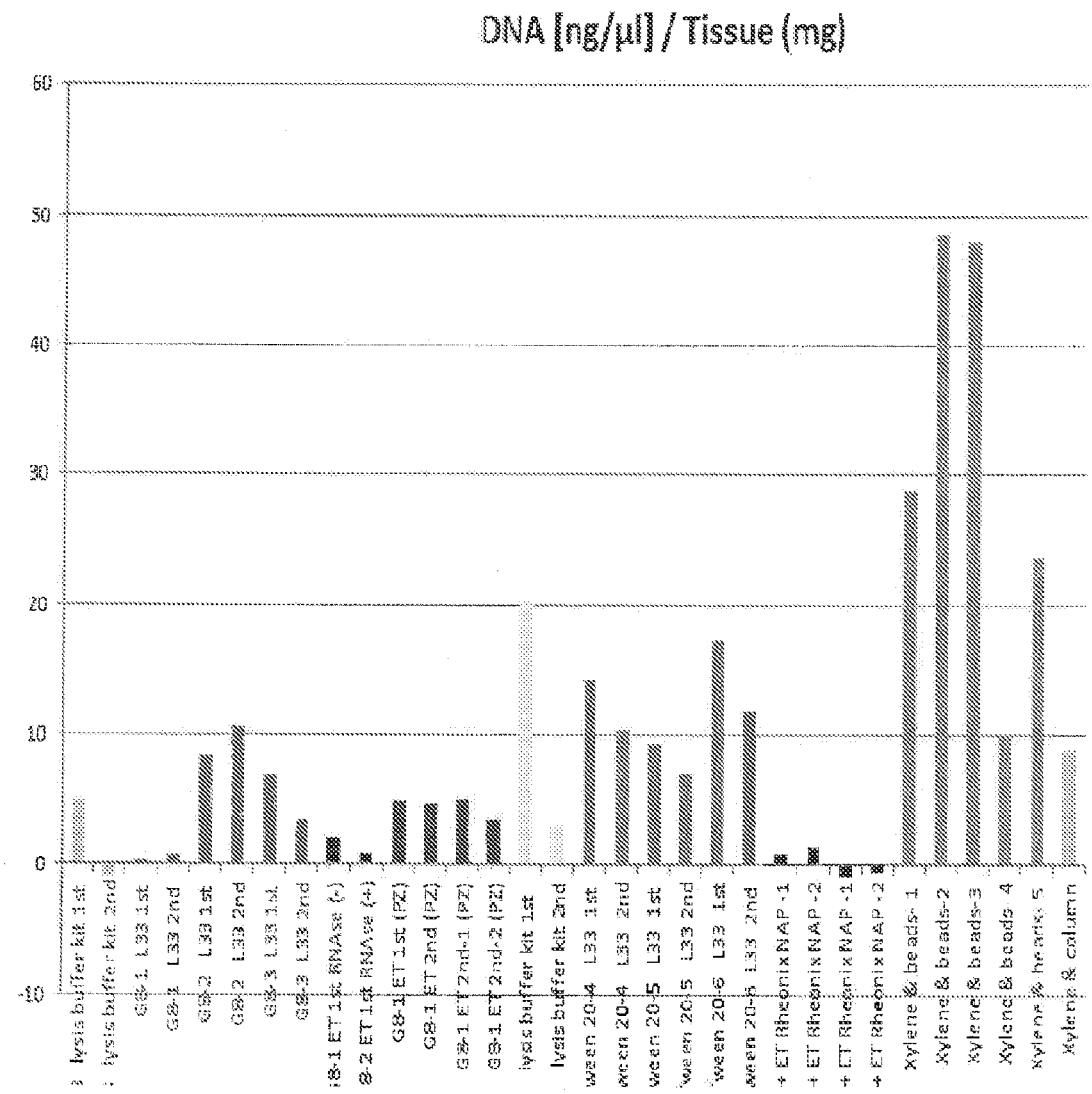
FIG. 8 shows quantitative results in nanograms per microliter of eluted DNA recovered from the embodied system/method, according to an illustrative embodiment of the invention.

FIG. 8 shows the quantity of DNA recovered using a microfluidic system that performs the liquid-liquid extraction followed by de-crosslinking, lysing and traditional silica based affinity capture of nucleic acids with later elution. The results compare the liquid-liquid extraction system using various buffers and surfactants to the traditional xylene extraction method The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

I claim:

1. A microfluidic method for preparing a tissue sample for nucleic acid purification, comprising:
   providing a formalin-fixed paraffin-embedded (FFPE) tissue sample in an aqueous solution having a density and a boiling point, in a vessel that contains a volume of liquid;
   providing a material selected from the group consisting of silicon oil, mineral oil and a solid silicone oil/wax mixture, having a density that is less than the density of the aqueous solution and a boiling point that is greater than the boiling point of the aqueous solution, in the vessel;

performing a nucleic acid purification step on the tissue sample; and performing a liquid-liquid extraction to remove the paraffin from the tissue sample prior to the nucleic acid purification step, wherein the liquid-liquid extraction step and the nucleic acid purification step are performed in a single microfluidic device.

2. The method of claim 1, further comprising providing a silicon oil as the immiscible liquid.

3. The method of claim 1, wherein the liquid-liquid extraction step further comprises raising the temperature of the aqueous solution in the vessel above the melting point of the paraffin embedding the tissue sample.

4. The method of claim 1, where the aqueous solution is a mixture of a chaotropic buffer and a surfactant.

5. The method of claim 4, further comprising adding a protein digesting enzyme to the aqueous solution following the removal of the paraffin from the tissue sample.

* * * * *